United States Patent [19]

Fraser et al.

[11] Patent Number: 5,410,059

[45] Date of Patent: Apr. 25, 1995

[54] TRANSITION METAL COMPLEXES HAVING 2,2'-BIPYRIDINE LIGANDS SUBSTITUTED BY AT LEAST ONE AMMONIUM ALKYL RADICAL

[75] Inventors: David Fraser, Nyon; Shaik M. Zakeeruddin; Michael Graetzel, both of Renens, all of Switzerland

[73] Assignee: Asulab S.A., Bienne, Switzerland

[21] Appl. No.: 166,977

[22] Filed: Dec. 14, 1993

[30] Foreign Application Priority Data

Dec. 15, 1992 [FR] France ................... 92 15214

[51] Int. Cl.[6] .................... C07F 15/00; C07F 15/02
[52] U.S. Cl. .................................................. 546/10
[58] Field of Search ........................................ 546/10

[56] References Cited

U.S. PATENT DOCUMENTS 5,162,508  11/1992  Lehn et al. ........................ 534/15

FOREIGN PATENT DOCUMENTS 8706706  11/1987  WIPO ................... 546/10
9212254   7/1992  WIPO ................... 546/10
9214741   9/1992  WIPO ................... 546/10
9214836   9/1992  WIPO ................... 546/10

OTHER PUBLICATIONS

Chemical Abstracts, vol. 111, No. 13, Abstract No. 125,629d, p. 713, Sep. 25, 1989.
Yonemoto et al, J. Am. Chem. Soc, vol. 114, No. 21, pp. 8081–8087, 1992.
Chemical Abstracts, vol. 104, No. 4, 27 Jan. 1986, Columbus Ohio, Abstract No. 26689x, G. Jones II et al.
Chemical Abstracts, vol. 113, No. 11, 10 Sep. 1990, Columbus Ohio, Abstract No. 98457d, A. J. Downard et al.
Chemical Abstracts, vol. 109, No. 12, 19 Sep. 1988, Columbus Ohio, Abstract No. 100637a, F. Daire et al.
Chemical Abstracts, vol. 111, No. 14, 2 Oct. 1989, Columbus Ohio, Abstract No. 125629d, V. E. Maier et al.
Chemical Abstracts, vol. 105, No. 16, 20 Oct. 1986, Columbus Ohio, Abstracts No. 141913y, F. Daire et al.
Chemical Abstracts, vol. 101, No. 17, 22 Oct. 1984, Columbus Ohio, Abstract No. 159978a S. Sahami et al.
Chemical Abstracts, vol. 116, No. 18, 4 May 1992, Columbus Ohio, Abstract No. 186612t, M. A. Hayes et al.
Chemical Abstracts, vol. 116, No. 20, 18 May 1992, Columbus Ohio, Abstract No. 203134h, C. P. Horwitz et al.
Chemical Abstracts, vol. 109, No. 25, 19 Dec. 1988, Colubus Ohio, Abstract No. 239126b, E. Garcia et al.

Primary Examiner—C. Warren Ivy
Assistant Examiner—Zinna N. Davis
Attorney, Agent, or Firm—Weil, Gotshal & Manges

[57] ABSTRACT

Complexes of the general formula I

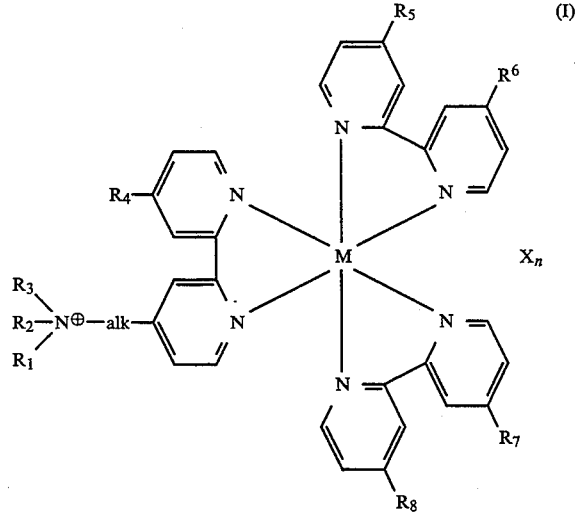

wherein $R_1$, $R_2$ and $R_3$, which may be the same or different, each represent a straight or branched alkyl radical having 1 to 5 carbon atoms or together with the adjacent nitrogen atom a heterocyclic radical having 5 to 7 carbon atoms; "alk" represents a straight or branched alkylene radical having 1 to 5 carbon atoms; $R_4$ to $R_8$, which may be the same or different, represent hydrogen, or a hydroxy, alkoxy, aryloxy or primary secondary or tertiary amino group, or the group -alk-N+ ($R_1R_2R_3$) wherein "alk", $R_1$, $R_2$ and $R_3$ have the meanings given above; M represents a transition metal such as Fe, Ru or Os; X represents an anion and n is an integer corresponding to the number of positive charges of the complex.

10 Claims, 2 Drawing Sheets

TRANSITION METAL COMPLEXES HAVING 2,2'-BIPYRIDINE LIGANDS SUBSTITUTED BY AT LEAST ONE AMMONIUM ALKYL RADICAL

FIELD OF THE INVENTION

The instant invention relates to a novel family of complexes of a Group VIII transition metal such as iron (II), ruthenium (II) or osmium (II), having three bidentate 2,2'-bipyridine ligands, at least one of the ligands being substituted by at least one quaternary ammonium alkyl group, as well as salts thereof.

The invention also relates to a process for the preparation of these new complexes.

By way of example of the use of the complexes, the invention also relates to the use of these compounds as mediators in redox reactions. These complexes have been found to be particularly useful in measuring the concentration of a compound in solution, and notably of glucose in a biological or physiological liquid, by acting as mediators for the transfer of electrons between one specific enzyme of said component, such as glucose oxidase (GOD) in the case of glucose, and a measurement electrode in a amperometric sensor.

DESCRIPTION OF THE PRIOR ART

According to R. SZENTRIMAY et al. (Electrochemical studies of biological systems—ch. 9 page 143-169—Am. Chem. Soc. Washington D.C. 1977), who established a list of criteria towards which an ideal mediator should tend, it is known that a mediator should notably have a well determined normal $E_o$ oxidoreduction potential in experimental conditions and a relatively rapid electron transfer rate $k_{med}$. In the case of glucose analysis, it is in particular desired to have a mediator with a constant $k_{med}$ greater than $1 \times 10^6$, $M^{-1} s^{-1}$ and a normal oxidoreductional potential $E_o$ that is as low as possible, preferably between $-400$ mV and $+400$ mV to reduce or eliminate the risks of interference with other compounds present in the solution to be analysed.

Numerous compounds have already been proposed as mediators in redox reactions, such as ferrocene and its derivatives [Cass A-E-G et coll. Anal.Chem. 56, 667-671 (1984)]. More recently, international application WO 92/14741 in the name of the applicant discloses a family of mono, bis or tris (2,2'-bipyridine substituted) complexes of a metal selected from iron, ruthenium, osmium or vanadium; in this family, the specific choice of a transition metal and of electron donor substituents on the ligands made it possible to favourably influence the stability of the mediator, the mediation rate constant $k_{med}$ and the normal oxydoreduction potential $E_o$.

BRIEF SUMMARY OF THE INVENTION

The new family of mediators according to the invention makes it possible to have an even more favourable mediation rate constant $k_{med}$, while still preserving a normal oxidoreduction potential $E_o$ included in the limits desired for an ideal mediator. In the event that the ligands are bidentate 2,2'-bipyridine ligands, the preferred compounds of the invention have the following general formula (I):

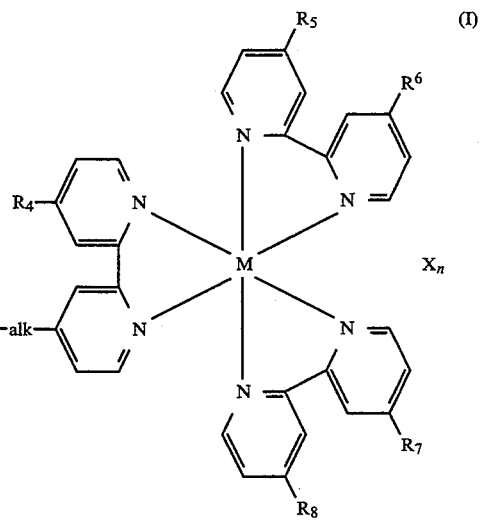

wherein $R_1$, $R_2$ and $R_3$, which may be the same or different, each represent a straight or branched alkyl radical having 1 to 5 carbon atoms or represent together with the adjacent nitrogen atom a heterocyclic radical having 5 to 7 carbon atoms; "alk" represents a straight or branched alkylene radical having 1 to 5 carbon atoms; $R_4$ to $R_8$, which may be the same or different, represent hydrogen, or a hydroxy, alkoxy,aryloxy, primary secondary or tertiary amino group or the group -alk-$N^+$ ($R_1R_2R_3$) wherein "alk", $R_1$, $R_2$ and $R_3$ have the meanings given above; M represents a transition metal such as iron; ruthenium or osmium; X represents an anion such as $Cl^-$, $PF_6^-$, $Br^-$, $BF_4^-$ and n is an integer corresponding to the total number of positive charges of the ligands and of the transition metal.

DETAILED DESCRIPTION OF THE INVENTION

In connection with novel chemical complexes, notably useful via synthesis of the complexes of formula I, the invention also relates to bipyridines substituted by at least one ammonium alkyl radical of general formula (II)

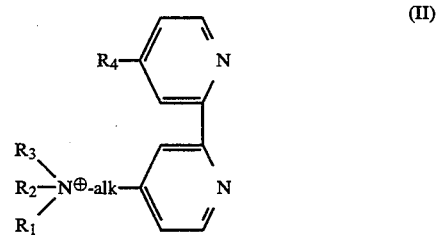

wherein $R_1$, $R_2$, $R_3$ and $R_4$ and "alk" have the same meanings as those given for general formula I.

According to a preferred embodiment, the invention relates to compounds wherein the alkylene radical "alk" represents the methylene radical $-CH_2-$.

According to another preferred embodiment, the invention relates to compounds wherein $R_4$ represents $N(R_1R_2R_3)$.

According to another preferred embodiment, the invention relates to compounds wherein the radical "alk" and $R_4$ have the meanings given above and $R_1$, $R_2$, $R_3$ represent the ethyl radical. The compounds of the present invention then have at least one 4,4'-bis(triethylammoniummethyl)-2,2'-bipyridine ligand and have the general formula III (III)

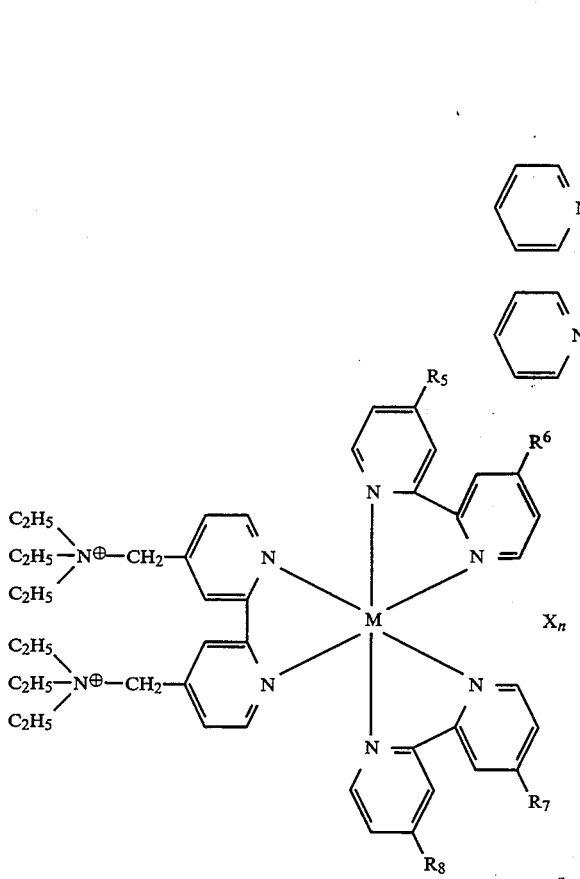

wherein $R_5$, $R_6$, $R_7$, $R_8$, X and n have the same meanings as those given for general formula I.

The preferred complexes of the present invention corresponding to general formula III are:
  the complex osmium bis [4,4'-bisamino-2,2'-bipyridine]mono[4,4'- bis (triethylammoniummethyl) -2,2'-bipyridine, hereinafter referred to as Os(DA-bpy)$_2$(TEAM-bpy) and salts thereof,
  the complex ruthenium bis [4,4'-bisamino-2,2'-bipyridine]mono[4,4'-bis(triethylammoniummethyl)-2,2'-bipyridine], hereinafter referred to as Ru(DA-bpy)$_2$(TEAM-bpy) and salts thereof,
  the complex ruthenium bis [4,4'-bis (dimethylamino2,2'-bipyridine]mono[4,4'-bis(triethylaminomethyl)-2,2'-bipyridine], hereinafter referred to as Ru(DA-bpy)$_2$ (TEAM-bpy) and salts thereof,
  the complex osmium bis[4,4'-bis(triethylammoniummethyl) 2,2'-bipyridine]mono[4,4'-bisamino)2,2'-bipyridine], hereinafter referred to as Os(TEAM-bpy)$_2$(DA-bpy) and salts thereof,
  the complex osmium tris[4,4'-bis(triethylammoniummethyl)-2,2'-bipyridine], hereinafter referred to as Os(TEAM-bpy)$_3$, and salts thereof,
  the complex iron tris[4,4'-bis(triethylammoniummethyl)-2,2'-bipyridine], hereinafter referred to as Fe(TEAM-bpy)$_3$, and salts thereof.

According to another preferred embodiment, the invention relates to compounds wherein the radical "alk" and $R_4$ have the meanings given above and $R_1$, $R_2$ and $R_3$ together form the radical N-pyridyl together with the adjacent nitrogen atom. The complexes of the present invention thus have at least one 4,4'-bis(N-pyridiniummethyl)-2,2'-bipyridine ligand and have the general formula IV (IV)

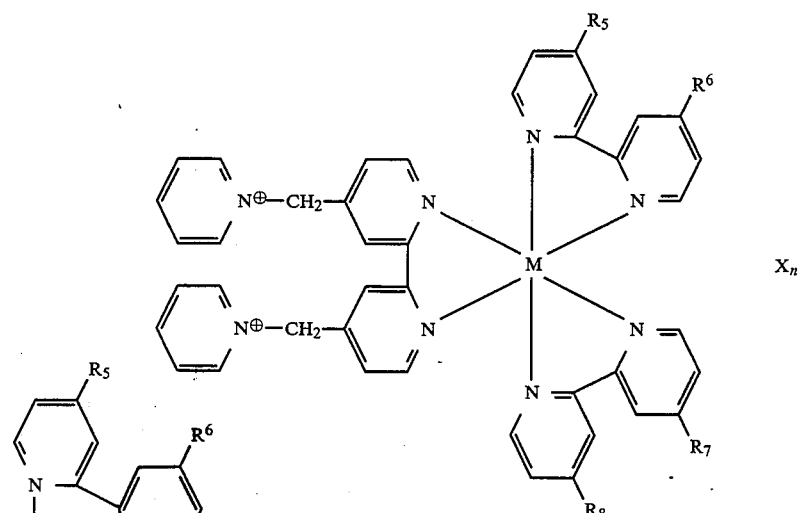

wherein $R_5$, $R_6$, $R_7$, $R_8$, X and n have the same meanings as those given for general formula I.

Preferred complexes of the present invention corresponding to general formula IV are:
  the complex osmium bis[4,4'-bisamino-2,2'-bipyridine]mono[4,4'-bis(N-pyridiniummethyl)-2,2,-bipyridine], hereinafter referred to as Os(DA-bpy)$_2$(NPM-bpy) and salts thereof,
  the complex ruthenium bis[4,4'-bisamino-2,2'-bipyridine]mono[4,4'-bis(N-pyridiniummethyl)2,2'-bipyridine], hereinafter referred to as Ru(DA-bpy)$_2$(NPM-bpy) and salts thereof,
  the complex osmium bis[4,4'-bis(N-pyridiniummethyl)-2,2'-bipyridine]mono(4,4'-bisamino-2,2'-bipyridine), hereinafter referred to as Os(NPM-bpy)$_2$(DA-bpy) and salts thereof,
  the complex osmium tris[4,4'-bis(N-pyridiniummethyl)-2,2'-bipyridine], hereinafter referred to as Os(NPM-bpy)$_3$, and salts thereof,
  the complex iron tris[4,4'-bis(N-pyridiniummethyl)-2,2'-bipyridine], hereinafter referred to as Fe(-TEAM-bpy)$_3$, and salts thereof.

According to another preferred embodiment, the invention relates to complexes of formula (I), (III) or (IV) wherein the transition metal M is osmium.

Compounds of general formulae I, II, III or IV correspond to the preferred complexes of the invention, wherein the bipyridine ligands are substituted in 4,4'-position, but it is clear that the compounds substituted in different positions are also included in the invention.

When the compounds of the present invention are used as redox mediators, a soluble salt such as the chloride or hexafluorophosphate should preferably be selected.

The general procedure to obtain compounds of the invention corresponding to the general formulae I, III or IV consists, in a first step, in preparing a compound of formula II having a ligand substituted by a quaternary ammonium radical by reacting a 4,4'-bis-bromoalkyl-2,2'-bipyridine with a tertiary amine in an excess of compounds of formula $N(R_1R_2R_3)$, wherein $R_1$, $R_2$ and $R_3$ have the meanings given for formula (I), in the presence of a suitable organic solvent by refluxing the solvent under a nitrogen atmosphere for about 3 hours and in isolating the compound of formula II obtained in conventional manner; then, in a second step, in reacting the complex of formula (II) with a substantially stoichiometric amount of a soluble salt of the complex formed by the metal M and the two bipyridine ligands substituted by $R_5$, $R_6$, $R_7$ and $R_8$ respectively, said salt having been previously prepared using known methods.

In the event that the substituents $R_4$ to $R_6$ represent $-N(R_1R_2R_3)$, the bis complex of a compound of formula (II) with a suitable metal M is first prepared and the compound obtained is then reacted with a suitable bipyridine substituted by $R_7$ and $R_8$ according to the second step of the general procedure.

In the event that the substituents $R_4$ to $R_6$ represent $-N(R_1R_2R_3)$, the process consists of heating at reflux of the solvent a solution containing the compound of formula (II) prepared in the first step and a soluble salt of the metal M in substantially stoichiometric proportions.

For all the compounds of the present invention, the presence of at least one permanent positive charge on at least one bipyridine ligand makes it possible to increase the overall positive total charge of the complexes up to values which it is not yet possible to obtain with formerly known mediators.

The invention will be better understood with reference to the examples given hereinbelow to illustrate the preparation and electrochemical properties of a representative number of compounds of the invention with view to an application as mediators in redox reactions permitting the volumetric analysis of a compound in solution in the presence of a suitable oxidoreductase enzyme.

Example 1

Preparation of the complex [Os (DA-bpy)$_2$(TEAM-bpy)](PF$_6$)$_4$ 4,4'-bis(triethylammoniummethyl)-2-2'-bipyridine bromide (hereinafter referred to as TEAM-bpy) was prepared in a first step. 4 g (11.7 mmol) of 4,4'-bromomethylbipyridine were dissolved in 16 ml of chloroform in a reaction vessel. 6 ml of triethylamine (59.4 mmol in excess) were added to this solution and the mixture was heated at reflux for at least 3 hours at about 45–50° C. under a nitrogen atmosphere at atmospheric pressure. The product was isolated by filtration, washed with chloroform and dried under high vacuum. The product obtained has the basic formula $C_{24}H_{40}N_4Br_2$ (3,03H$_2$O) and its elementary analysis is:

|  | C % | H % | N % | H$_2$O |
|---|---|---|---|---|
| calculated | 48.1 | 7.75 | 9.35 | 9.11 |

-continued

|  | C % | H % | N % | H$_2$O |
|---|---|---|---|---|
| found | 46.51 | 7.49 | 9.32 | 9.12 |

NMR analysis in a solution of D$_2$O corresponds to the following spectrum:

1.5(t); 3.4(q); 4.65 (s); 7.8(dd); 8.3(d); 8.9(d)

In a second step 0.053 g (0.097 mmol) of TEAM-bpy was dissolved in 0.5 ml water and then 10 ml ethylene glycol and 0.05 g (0.075 mmol) of osmium bis(4,4'-bisamino-2,2'-bipyridine)Cl$_2$ (hereinafter referred to as Os(DA-bpy)$_2$Cl$_2$ were added and the mixture heated at reflux for at least 4 hours at about 140°–150° C. under a nitrogen atmosphere at atmospheric pressure until a brown coloration appeared. After cooling at room temperature, the reaction medium was poured into a separating funnel and the product precipitated from ethylene glycol by adding 20 ml of diethylether and 5 ml of acetone, by eliminating the ether phase and repeating the operation until visible precipitation of the compound of this example. The complex was isolated by filtration and dissolved in 10 ml water; addition of an aqueous solution of potassium hexafluorophosphate precipitated the complex in the form of its hexafluorophosphate salt; it was isolated by filtration, washed with water and then diethylether and dried under a high vacuum.

Example 2

Preparation of the Complex [Ru (DA-bpy)$_2$(NPM-bpy)](PF$_6$)$_4$

The compound 4,4'-bis(N-pyridiniummethyl)-2-2'-bipyridine (hereinafter referred to as NPM-bpy) was prepared in a first step. 4 g (11.7 mmol) of 4,4'-bromoethylbipyridine) were dissolved in 15 ml of chloroform in a reaction vessel. 6 ml of pyridine (75 mmol in excess) were added to this solution and the mixture was heated at reflux for at least 3 hours at about 45°–50° C. in a nitrogen atmosphere at atmospheric pressure. The product was isolated by filtration, washed with chloroform and dried under high vacuum. NMR analysis of the compound obtained in a solution of D$_2$O corresponds to the following spectrum:

6.1(s); 7.55(dd); 8.15 (d); 8.25(d); 8.65(t); 8.75(8D); 9.05 (dd)

In a second step 0,028 g (0.050 mmol) of NPM-bpy was dissolved in 5 ml water and then 10 ml of dimethylformamide and 0,025 g (0,043 mmol) of ruthenium bis(4,4'-bisamino-2,2'-bipyridine) Cl$_2$ (hereinafter referred to as Ru(DA-bpy)$_2$Cl$_2$) were added and the mixture heated at reflux for at least 4 hours at about 140°–150° C. under a nitrogen atmosphere at atmospheric pressure. After having allowed the mixture to cool to room temperature, the solution was filtered and the solvent concentrated to a quarter of the original volume. The complex was then precipitated by addition of diethylether, the complex was isolated by filtration and dissolved in 10 ml water; the complex was precipitated in the form of its hexafluorophosphate salt by addition of an aqueous solution of potassium hexafluorophosphate; it was isolated by filtration, washed with diethylether and dried under a high vacuum.

EXAMPLE 3

Preparation of the Complex [Os(TEAM-bpy)$_2$(DA-bpy)](PF$_6$)$_6$ 0.221 g (0.406 mmol) of TEAM-bpy prepared as stated in the first step of Example 1 was dissolved in a reaction vessel in 1 ml of water and then 10 ml of ethylene glycol were added and then 0.10 g (0.203 mmol) of K$_2$OsCl$_6$ salt was added and the mixture heated at reflux for at least ninety minutes in a nitrogen atmosphere at an atmospheric pressure of about 140°–150° C. Then, after having precipitated and isolated the complex and returned it to solution 0.042 g (0.225 mmol) of 4,4'-bisamino-2,2'-bipyridine were added and the reaction medium was heated at reflux at about 140°–150° C. for at least 90 minutes in a nitrogen atmosphere at atmospheric pressure until appearance of a brown coloration. The complex obtained was then precipitated, isolated, washed and dried as described in Example 1.

EXAMPLE 4

Preparation of the Complex [Os(NPM-bpy)$_2$(DA-bpy)](PF$_6$)$_6$

The compound of this example was obtained by following the process described in Example 1, but by using NPM-bpy as prepared in the first step of Example 2.

EXAMPLE 5

Preparation of the Complex [Os(TEAM-bpy)$_3$](PF$_6$)$_8$ 0.183 g (0.337 mmol) of TEAM-bpy prepared as indicated in the first step of Example 1 was dissolved in a reaction vessel in 1 ml water, 10 ml ethylene glycol were then added and then 0.05 g (0.101 mmol) of K$_2$OsCl$_6$ and the mixture was heated at reflux for about 140°–150° C. for at least 5 hours under nitrogen atmosphere and at atmospheric pressure until appearance of a brown coloration. After cooling the product of this example was precipitated from ethylene glycol using the method described in the second step of Example 1. After isolation of the complex in the form of hexafluorophosphate a compound was obtained having the basic formula:

$$C_{72} H_{120} N_{12} Os P_6 F_{48}$$

and the elementary analysis

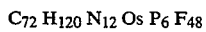

|  | C % | H % | N % |
|---|---|---|---|
| calculated | 34.54 | 4.83 | 6.71 |
| found | 38.44 | 4.16 | 6.48 |

EXAMPLE 6

Preparation of the Complexes [RuDMA-bpy)$_2$(TEAM-bpy)](PF$_6$)$_4$ and [RU(DA-bpy)$_2$(TEAM-bpy)](PF$_6$)$_4$ The complex [Ru(DMA-bpy)$_2$(TEAM-bpy)](PF$_6$)$_4$ was obtained by following the procedure described in Example 2, but starting from TEAM-bpy and Ru (4,4'-dimethylamino-2,2'-bipyridine) Cl$_2$; the complex [Ru(-DA-bpy)$_2$(TEAM-bpy)](PF$_6$)$_4$ was likewise obtained starting from TEAM-bpy and Ru(DA-bpy )$_2$Cl$_2$.

EXAMPLE 7

Preparation of the Complex [Os(DA-bpy)$_2$(NPM-bpy)](PF$_6$)$_4$

The compound of this example was obtained by following the process described in Example 1, but starting from NPM-bpy, as prepared in the first step of Example 2, and from Os(DA-bpy)$_2$Cl$_2$.

EXAMPLE 8

Preparation of [Os(NPM-bpy)$_3$](PF$_6$)$_8$ and [Fe(TEAM-bpy)$_3$](PF$_6$)$_8$

The complex [Os(NPM-bpy)$_3$](PF$_6$)$_8$ was obtained by following the process described in Example 5, but starting from NPM-bpy; similarly, [Fe(TEAM-bpy)$_3$](PF$_6$)$_8$ and [Fe(NPM-bpy)$_3$](PF$_6$)$_8$ were obtained starting from TEAM-bpy in the presence of FeCl$_2$,4H$_2$O.

The complexes of Examples 1 to 8 have moreover been characterised by their UV and visible light absorption spectrum which presents the specific band of the metalligand bonds in the region of 500 nm. The following table gives the wavelength of the maximum and the value of the coefficient of extinction for each of the compounds.

TABLE I

| Complexe | $\lambda_{max}$ (nm) | $\epsilon$ (M$^{-1}$cm$^{-1}$) |
|---|---|---|
| [Os(DA-bpy)$_2$ (TEAM-bpy)] (PF$_6$)$_4$ | 556 | 8743 |
| [Os(DA-bpy)$_2$ (NPM-bpy)] (PF$_6$)$_4$ | 536 | 10818 |
| [Os(TEAM-bpy)$_2$ (DA-bpy)] (PF$_6$)$_6$ | 512 | 9428 |
| [Os(NPM-bpy)$_2$ (DA-bpy)] (PF$_6$)$_6$ | 516 | 11054 |
| [Os(TEAM-bpy)$_3$] (PF$_6$)$_8$ | 492 | 7364 |
| [Os(NPM-bpy)$_3$] (PF$_6$)$_8$ | 494 | 10449 |
| [Ru(DA-bpy)$_2$ (TEAM-bpy)] (PF$_6$)$_4$ | 526 | 10559 |
| [Ru(DA-bpy)$_2$ (Npm-bpy)] (PF$_6$)$_4$ | 530 | 8593 |
| [Ru(DMA-bpy)$_2$ (TEAM-bpy)] (PF$_6$)$_4$ | 506 | 9296 |
| [Fe(TEAM-bpy)$_3$] (PF$_6$)$_8$ | 534 | 17375 |
| [Fe(NPM-bpy)$_3$] (PF$_6$)$_8$ | 533 | 9845 |

The potentiodynamic activity of the compounds of the invention and their ability to act as redox mediator have been evaluated by conventional cyclic voltametric methods making it possible to determine the normal E$_o$ oxydoreduction potential, the k$_{med}$ constant and the electrochemical behaviour of the complex.

In a first method the complex (5.10$^{-4}$ M) was dissolved in an organic solvent (acetonitrile containing LiClO$_4$ 0.2 M), or in a phosphate buffer PBS (NaCl 50 mM, NaH$_2$PO$_4$ 5 mM adjusted to pH 7.4). A scan was then conducted at a constant rate (25 mV.s-1) by using a vitreous carbon electrode as working electrode and a calomel electrode (SCE) as reference electrode, maintaining the measurement cell under a current of nitrogen.

In a second method, more particularly designed to display the mediator properties of the complexes for glucose analysis in the presence of a GOD enzyme oxidase, phosphate buffer PBS was used by replacing the vitreous carbon working electrode by a spectroscopic graphite electrode onto which the complex to be studied had been adsorbed.

The same measurements were carried out using as reference compound the complex osmium or ruthenium bis (4,4'-bisamino-2,2'- bipyridine) mono (4,4'-dimethyl-2,2'-bipyridine) (hereinafter referred to as Os(DA-bpy)$_2$(dm-bpy) and Ru(DA-bpy)$_2$(dm-bpy); these complexes do indeed have structures close to those of the complexes of the invention, but do not have any quaternary ammonium substituent.

These measurements have made it possible to determine the normal $E_o$ oxidoreduction potential in different conditions, and the mediation rate constant $k_{med}$.

BRIEF DESCRIPTION OF THE DRAWINGS

These measurements are set out hereinafter in more detailed manner with reference to the complex [Os(-DA-bpy)2(TEAM-bpy)](PF$_6$)$_4$ taken by way of example. The value $E°_{CH_3CN}=240$ mV was obtained for the oxidoreduction potential in an organic solvent. In a phosphate buffer PBS an $E°_{PBS}-50$ mV oxidoreduction potential and a voltamogram corresponding to FIG. 1 were obtained. The kinetic measurements carried out correspond to a $k_{med}$ constant$=1.5 \cdot 10^7$ $_m-1$ $_s-1$ (according to the method of R. S. Nicholson and I. Shain, Anal. Chem., 76 (1964) 706).

The voltamogram of FIG. 2 was obtained using the same measurements in a phosphate buffer PBS, but after adsorption on a spectroscopic graphite electrode wherein the curve in dotted lines corresponds to the measurements carried out in the presence of glucose (100 mM) and the curve shown in a straight line in the absence of glucose. After adsorption of the mediator its redox potential becomes positive, as is often observed and corresponds to the value $E°_{ads}=180$ mV.

Finally.

Figure 1:
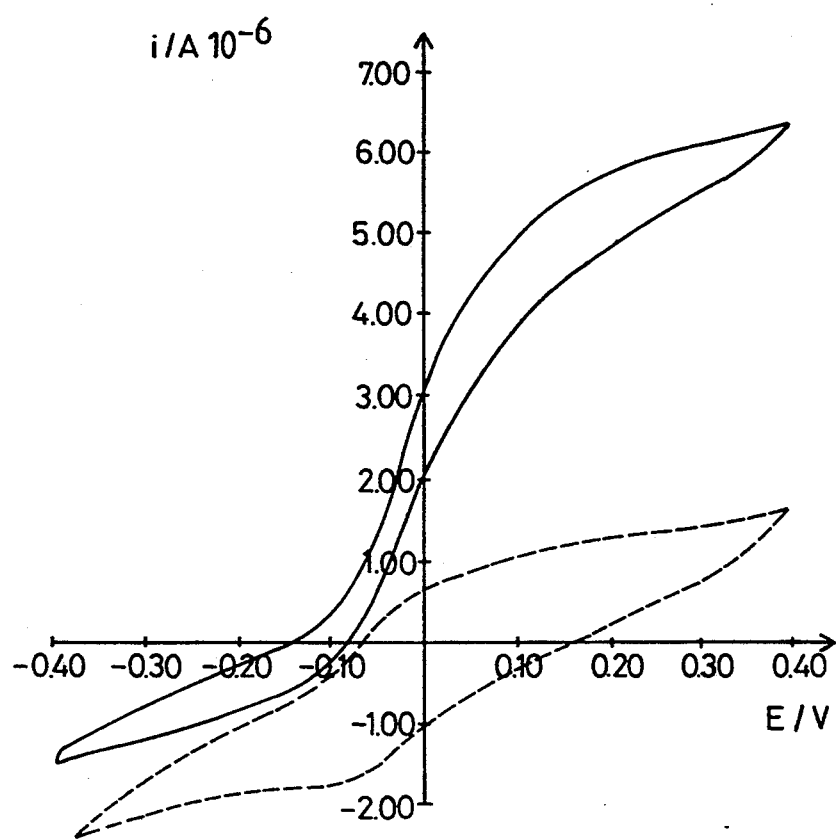
Figure 2:
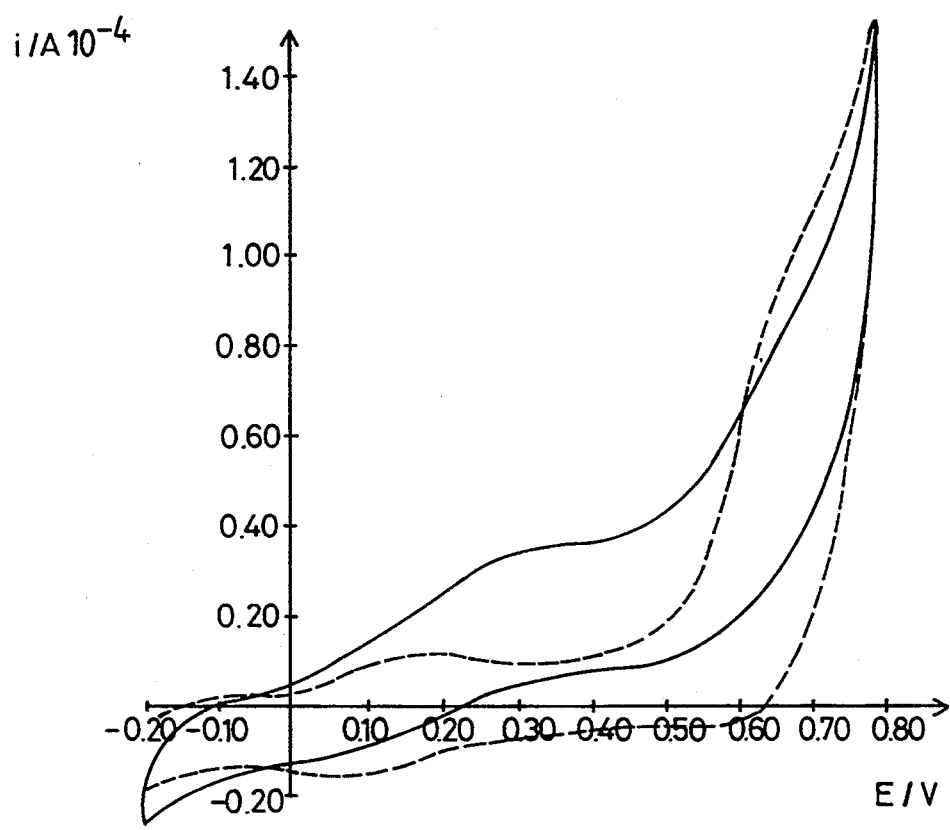
Figure 3:
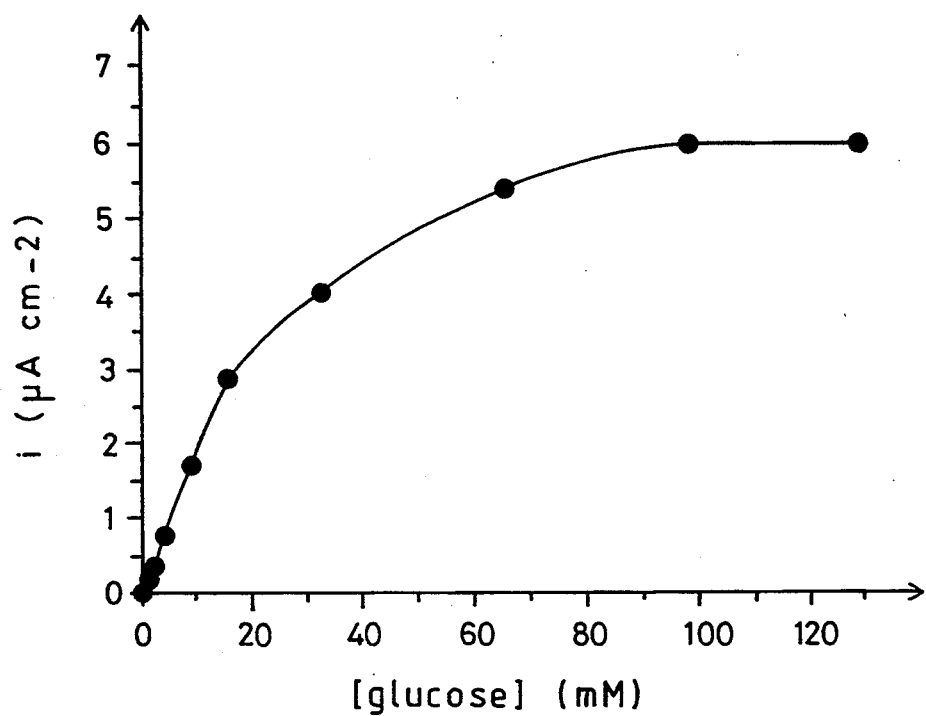
FIG. 3 shows by way of illustration the curve obtained when a constant potential of 200 mV is applied and the glucose concentration is varied. This curve shows that one obtains excellent linearity up to almost 20 mM.

The measurements carried out with other complexes of the invention are shown in the following Table II, by comparison with the two above mentioned reference compounds.

TABLE II

| Complexe | $E°_{CH_3CN}$ (mV) | $E°_{PBS}$ (mV) | $E°_{ads}$ (mV) | $k_{med}$ ($M^{-1}s^{-1}$) |
|---|---|---|---|---|
| [Os(DA-bpy)$_2$(TEAM-bpy)] (PF$_6$)$_4$ | 240 | −50 | 180 | $1,5 \cdot 10^7$ |
| [Os(DA-bpy)$_2$(NPM-bpy)] (PF$_6$)$_4$ | 170 | −50 | 55 | $1,4 \cdot 10^7$ |
| [Os(TEAM-bpy)$_2$(DA-bpy)] (PF$_6$)$_6$ | 400 | 270 | 430 | $4,0 \cdot 10^5$ |
| [Os(NPM-bpy)$_2$(DA-bpy)] (PF$_6$)$_6$ | 350 | 300 | 650 | $1,0 \cdot 10^6$ |
| [Os(TEAM-bpy)$_3$] (PF$_6$)$_8$ | 790 | 610 | 655 | $1,0 \cdot 10^5$ |
| [Os(NPM-bpy)$_3$] (PF$_6$)$_8$ | 790 | 630 | n.d. | n.d. |
| [Ru(DA-bpy)$_2$(TEAM-bpy)] (PF$_6$)$_4$ | 680 | 550 | 555 | $3,0 \cdot 10^6$ |
| [Ru(DA-bpy)$_2$(NPM-bpy)] (PF$_6$)$_4$ | 670 | 530 | 530 | $3,7 \cdot 10^6$ |
| [Ru(DMA-bpy)$_2$(TEAM-bpy)] (PF$_6$)$_4$ | 510 | 410 | 460 | $1,3 \cdot 10^6$ |
| [Fe(TEAM-bpy)$_3$] (PF$_6$)$_8$ | 1170 | 1180 | n.d. | n.d. |
| [Fe(NPM-bpy)$_3$] (PF$_6$)$_8$ | 1075 | 975 | n.d. | n.d. |
| [Os(DA-bpy)$_2$(dm-bpy)] Cl$_2$ | 120 | −60 | 65 | $6,7 \cdot 10^6$ |
| [Ru(DA-bpy)$_2$(dm-bpy)] Cl$_2$ | 600 | 410 | 450 | $1,0 \cdot 10^6$ |

These results show that the compounds of the invention having a ligand substituted by a quaternary ammonium, that is having an overall positive charge of +5 have a mediation rate very superior to that of the closest non-substituted homologs, bearing a global charge of +3. For example the complex Os(DA-bpy)2(TEAM-bpy) has a constant $k_{med}=1.5 \cdot 10^7 M^{-1}s^{-1}$ about 2 times higher than that of Os(DA-bpy)2(dm-bpy) and for Ru(-DA-bpy)2(dm-bpy) there also exists a factor 3 between the two constants $k_{med}$ of the mediation rate. The oxidoreduction potential is rather low for all these compounds. For the complexes Os(DA-bpy)2(TEAM-bpy) and Os(DA-bpy)2(NPM-bpy) it is also noted that the constants $k_{med}$ and $E_o$ have virtually the same value: the nature of the quaternary ammonium substituent (TEAM or NPM) does not notably influence the properties of the complex. Complexes having a maximum positive global charge—for example +9 for Os(-TEAM-bpy)3—have values of constants a little less favourable for application as mediator for glucose analysis in the presence of glucose oxidase; these complexes may nonetheless be interesting as mediators for analysing a component other than glucose in solution in the presence of a different specific enzyme having characteristics different to those of glucose oxidase GOD.

This set of properties thus makes it possible to use the complexes of the invention as redox mediators for the analysis of a component in solution in the presence of an enzyme specific to said component. They have proved of particular interest for the analysis of glucose in the presence of the enzyme glucose oxidase (GOD).

We claim:

1. A transition metal complex having three bidentate ligands at least two of which are substituted in the 4,4' position by quaternary ammonium alkyl groups with the formula

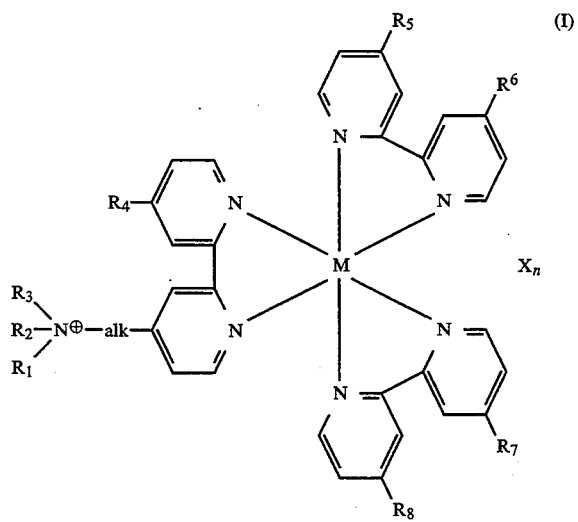

wherein $R_1$, $R_2$, and $R_3$ may be the same or different and each represents a straight chain or branched chain alkyl group having 1 to 5 carbon atoms or taken together with the adjacent nitrogen atom represent a heterocyclic radical having 5 to 7 carbon atoms; alk represents a straight chain or branched alkylene radical having 1 to 5 carbon atoms; $R_4$ represents the group -alk-N+$R_1R_2R_3$ wherein alk, $R_1$, $R_2$, and $R_3$ have the meanings given above; $R_5$ to $R_8$, which may be the same or different, represent hydrogen, or a hydroxy, alkoxy, aryloxy or primary, secondary or tertiary amino group or the group -alk-N+($R_1R_2R_3$) wherein alk, $R_1$, $R_2$, and $R_3$ have the meanings given above; M represents a transition metal selected from iron, ruthenium or osmium; x represents an anion selected from Cl, PF$_6$−, BR−, or BF$_4$− and n is an integer corresponding to the number of positive charges of the ligands and of the transition metal.

2. A complex according to claim 1 wherein the alkylene radical alk represents a methylene radical -CH$_2$-.

3. A complex according to claim 1 wherein -N(R$_1$R$_2$R$_3$) represents the triethylammonium group and corresponds to the formula III (III)

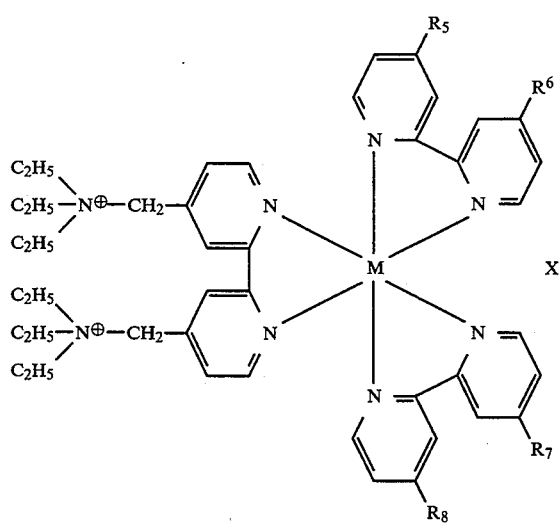

wherein R$_5$, R$_6$, R$_7$, R$_8$, X and n have the same meanings as those given for the general formula I.

4. A complex according to claim 3 which corresponds to one of the compounds of formula
  osmium bis[4,4'-bisamino-2,2'-bipyridine]-mono[4,4'-bis(triethylammoniummethyl)-2,2'-bipyridine, hereinafter referred to as Os(DA-bpy)$_2$(TEAM-bpy) or salts thereof,
  ruthenium bis[4,4'-bisamino-2,2'-bipyridine 4,4'-bis(-triethylammoniummethyl)-2,2'-bipyridine, hereinafter referred to as Ru(DA-bpy)$_2$(TEAM-bpy) or salts thereof,
  ruthenium bis[4,4'-bis(dimethylamino-2,2'-bipyridine]mono[4,4'-bis(triethylammoniummethyl)-2,2'-bipyridine], hereinafter referred to as Ru(DMA-bpy)$_2$(TEAM-bpy) or salts thereof,
  osmium bis[4,4'-bis(triethylammoniummethyl) 2,2'-bipyridine]mono[4,4'-bisamino) 2,2'-bipyridine, hereinafter referred to as Os(TEAM-bpy)$_2$(DA-bpy) or salts thereof,
  osmium tris [4,4'-bis(triethylammoniummethyl)-2,2'-bipyridine], hereinafter referred to as Os(TEAM-bpy)$_3$, or salts thereof,
  iron tris [4,4'-bis(triethylammoniummethyl)-2,2'-bipyridine], hereinafter referred to as Fe(TEAM-bpy)$_3$, or salts thereof.

5. A complex according to claim 1 wherein -N(R$_1$R$_2$R$_3$) represents the N-pyridino group and has the formula IV (IV)

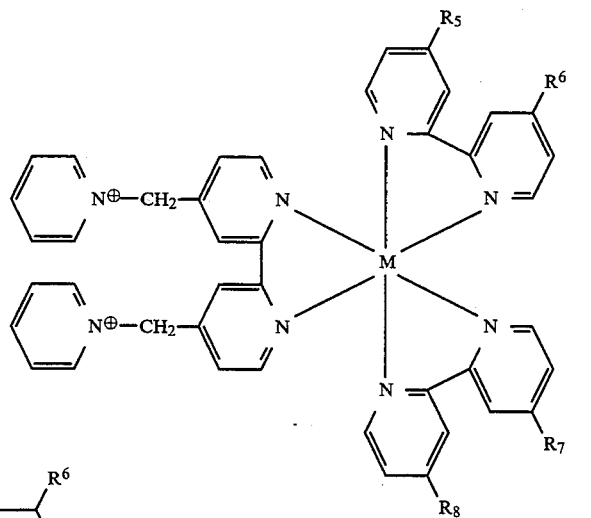

wherein R$_5$, R$_6$, R$_7$, R$_8$, X and n have the same meanings as those given for formula I.

6. A complex according to claim 5, which corresponds to one of the compounds of formula
  osmium bis[4,4'-bisamino-2,2'-bipyridine]-mono[4,4'-bis(N-pyridiniummethyl)-2,2'-bipyridine], hereinafter referred to as Os(DA-bpy)$_2$(NPM-bpy) or salts thereof,
  ruthenium bis[4,4'-bisamino-2,2'-bipyridine]-mono[4,4'-bis(N-pyridiniummethyl)-2,2'-bipyridine, hereinafter referred to as Ru(DA-bpy)$_2$(NPM-bpy) or salts thereof,
  osmium bis[4,4'-bis(N-pyridiniummethyl)-2,2'-bipyridine]mono[4,4'-bisamino-2,2'-bipyridine), hereinafter referred to as Os(NPM-bpy)$_2$(DA-bpy) or salts thereof,
  osmium tris [4,4'-bis(N-pyridiniummethyl) 2,2'-bipyridine], hereinafter referred to as Os(NPM-bpy)$_3$, or salts thereof,
  iron tris [4,4'-bis(N-pyridiniummethyl)-2,2'-bipyridine], hereinafter referred to as Fe(TEAM-bpy)$_3$, or salts thereof.

7. A complex according to claim 1 wherein the transition metal is osmium.

8. A complex according to claim 1 wherein the transition metal is ruthenium.

9. A complex according to claim 1 wherein the transition metal is iron.

10. A complex according to claim 1 wherein the salt is a chloride or a hexafluorophosphate.

* * * * *